United States Patent
Cook et al.

(10) Patent No.: US 9,648,945 B2
(45) Date of Patent: May 16, 2017

(54) SYSTEM FOR OPERATING MODES FOR AN ELECTRIC TOOTHBRUSH

(71) Applicant: KONINKLIJKE PHILIPS N.V., Eindhoven (NL)

(72) Inventors: Charles B. Cook, Seattle, WA (US); Joseph W. Grez, North Bend, WA (US); Wolter F. Benning, Seattle, WA (US); Christopher Dabrowski, Lynnwood, WA (US); Rick Peterson, Issaquah, WA (US); Gregg Heard, Amsterdam (NL); Martyn Gray Darnbrough Beedham, Amsterdam (NL); Hanne Lindholt Caspersen, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 143 days.

(21) Appl. No.: 14/269,519

(22) Filed: May 5, 2014

(65) Prior Publication Data

US 2014/0324226 A1    Oct. 30, 2014

Related U.S. Application Data

(62) Division of application No. 12/297,656, filed as application No. PCT/IB2007/001047 on Apr. 20, 2007, now Pat. No. 8,789,227.

(Continued)

(51) Int. Cl.
*A61C 17/22*    (2006.01)
*A46B 15/00*    (2006.01)
*A46B 5/00*    (2006.01)

(52) U.S. Cl.
CPC ...... *A46B 15/0002* (2013.01); *A46B 15/0006* (2013.01); *A46B 15/0008* (2013.01);
(Continued)

(58) Field of Classification Search
CPC .......................... A46B 15/0002; A61C 17/221
(Continued)

(56) References Cited

U.S. PATENT DOCUMENTS 3,998,234 A    12/1976 Stubbmann
4,428,091 A    1/1984  Janssen
(Continued)

FOREIGN PATENT DOCUMENTS

CN    2185112 Y    12/1994
DE    4439835 C1   2/1996
(Continued)

OTHER PUBLICATIONS

"Oral-B Sonic Complete", http://oralb.com/SonicComplete.
(Continued)

*Primary Examiner* — Laura C Guidotti

(57) ABSTRACT

Various operational mode arrangements of an electric toothbrush (10) include pre-programming a controller portion (16) of the electric toothbrush such that a single brushing event of approximately two minutes comprises automatically at least two different operating modes and specified times for each mode. Another operational mode includes the capability of operating the on/off button (20) of the toothbrush within a specified short time following termination of a normal brushing event to provide the user a specified additional time, e.g. 30 seconds of toothbrush action. A special toothbrush interface arrangement includes a display (80) which encourages children to maintain brushing for the full brushing period. This is accomplished through sequential illustration of the progress of an article from an initial state to a final desired state as the toothbrush is used for increasing portions of a full brushing time period. In another embodiment, a toothbrush (120) includes a capability of (Continued)

adjusting the performance/operating characteristics in accordance with the age of a child user.

7 Claims, 12 Drawing Sheets

Related U.S. Application Data

(60) Provisional application No. 60/793,902, filed on Apr. 20, 2006.

(52) U.S. Cl.
CPC ...... *A46B 15/0044* (2013.01); *A46B 15/0087* (2013.01); *A61C 17/221* (2013.01); *A46B 5/00* (2013.01); *A61C 2203/00* (2013.01)

(58) Field of Classification Search
USPC .................................................. 15/21.1–28
See application file for complete search history.

(56) References Cited

U.S. PATENT DOCUMENTS

| | | | |
|---|---|---|---|
| 5,544,382 A | 8/1996 | Giuliani et al. | |
| 5,570,325 A | 10/1996 | Arpadi | |
| 5,930,858 A | 8/1999 | Jung | |
| 5,943,723 A | 8/1999 | Hilfinger et al. | |
| 6,042,383 A | 3/2000 | Herron | |
| 6,611,780 B2 | 8/2003 | Lundell et al. | |
| 6,798,169 B2 | 9/2004 | Stratmann et al. | |
| 6,850,167 B2 | 2/2005 | Rosen | |
| 2002/0058239 A1 | 5/2002 | Wang | |
| 2002/0133308 A1 | 9/2002 | Lundell et al. | |
| 2003/0017874 A1 | 1/2003 | Jianfei et al. | |
| 2004/0134000 A1 | 7/2004 | Hilfinger et al. | |
| 2004/0177458 A1 | 9/2004 | Chan et al. | |
| 2007/0157404 A1 | 7/2007 | Brewer et al. | |
| 2008/0313829 A1 | 12/2008 | Dabrowski | |

FOREIGN PATENT DOCUMENTS

| | | |
|---|---|---|
| JP | H06315413 A | 11/1994 |
| JP | 2001346816 | 12/2001 |
| JP | 2002251372 A | 9/2002 |
| JP | 2003501137 A | 1/2003 |
| JP | 2004041684 A | 2/2004 |
| JP | 2004065838 A | 3/2004 |
| JP | 2005152217 A | 6/2005 |
| JP | 2006081155 A | 3/2006 |
| JP | 2003534095 | 5/2012 |
| WO | 2007072430 | 6/2007 |

OTHER PUBLICATIONS

"Oral-B Triumph Professional Care", http://oralb.com/product.
"Programmable Quadpacer", http://.sonicare.com/owners/b_features/b4_pq.asp.

SYSTEM FOR OPERATING MODES FOR AN ELECTRIC TOOTHBRUSH

CROSS REFERENCE TO RELATED CASES

This application is a divisional of co-pending U.S. patent application Ser. No. 12/297,656, filed Feb. 9, 2009 which is a U.S. National Stage Application under 35 U.S.C. §371 of International Application No. PCT/IB2007/001047, filed Apr. 20, 2007 and U.S. Provisional Ser. No. 60/793,902 filed Apr. 20, 2006.

BACKGROUND OF THE INVENTION

This invention relates generally to operational control of an electric toothbrush, and more specifically concerns the use and selection of various operational modes for an electric toothbrush.

Some electric toothbrushes have multiple modes of operation which may be selected by a user via control buttons on the body of the toothbrush, the control buttons generally referred to as a "user interface". Each mode will typically have a different brushing action; for instance, a normal mode may be particularly adapted for normal brushing/cleansing of the teeth, while a gentle mode might have an action which has less brush movement and/or moves at a slower rate. Another mode could be a massage mode in which the brush has a pulsing action.

These modes are illustrative only of the various mode possibilities. Typically, an operating mode, once selected, will control the operation of the toothbrush for an entire brushing event, i.e. for two minutes. If it is desired by a particular user to combine different modes within a single event time, i.e. two or more modes within a two-minute time, the user must manipulate the user interface controls to create such a specific mode/time profile manually every time that particular profile is desired. This is often too complex or inconvenient for a user to consistently and reliably accomplish. Hence, there is a need for simple controls to result in complex brushing profiles for a single brushing event. Such controls could be particularly desirable for those mode/time profiles which are known to produce beneficial effects. It would be advantageous for the users to have such a desirable profile available to them by a simple, straightforward control operation.

In addition, it is often desirable to have a simple means to extend the brushing time by a selected short period of time, i.e. 30 seconds. Typically, this is accomplished at the present time is by simply pushing the on/off button again following termination of the normal event, and then terminating the brushing manually when the desired additional time of brushing has elapsed. This, however, is often difficult to monitor.

Lastly, there are some special brushing circumstances such as encouraging children to brush appropriately and for a full desired time, which may be enhanced by a specialized brush arrangement which could be broadly categorized as a particular mode of operation. Also, it would be desirable to maintain a record of children's brushing with a convenient readout for parental monitoring of children's brushing patterns.

It is thus desirable that an electric toothbrush be arranged and adapted to provide an increased operating mode capability, while being simple in mode selection, thereby increasing the beneficial use of the electric toothbrush for the user.

SUMMARY OF THE INVENTION

Accordingly, disclosed herein is a system for operating an electric toothbrush in more than one mode of operation during a brushing event, comprising: an electric toothbrush with a toothbrush body, a brushhead, a motor for driving the brushhead and a controller for the motor, the controller being pre-programmed to produce at least one mode/time profile of operation in which the toothbrush operates in one operational mode for one selected time and then automatically changes, in accordance with a program, to at least one other operational mode for another selected time, different than the first operational mode, during a single brushing event, wherein the selected times for the operational modes add up to the time of a single brushing event; and a user interface operable by a user to initiate the mode/time profile operation.

Also disclosed is a system for extending the time of automatic operation of an electric toothbrush, comprising: a control system for the toothbrush which controls the operation of a brushhead portion of the toothbrush, the control system having a pre-programmed capability of providing a selected amount of additional time for operation of the toothbrush substantially immediately subsequent to the termination of a brushing event, the additional time being substantially less than the time of a single brushing event.

Also disclosed is a system to encourage brushing by children who are using an electric toothbrush, comprising: a display device for a power toothbrush which is in use, the display device including a display program in which a selected article progresses visually from an initial state to a final desired state as use of the toothbrush continues from the time it is turned on to the end of a desired time period for a brushing event.

Also disclosed is a system for adjusting operating characteristics of a power toothbrush for use by children at various ages, comprising: a power toothbrush responsive to instructions from an internal or external source to adjust operating characteristics of the toothbrush carried out by a control system, associated with a selected age of a child user; and an entry system for initiating operation of the power toothbrush at a selected level of operating characteristics.

DETAILED DESCRIPTION OF THE INVENTION

As indicated above, many electric toothbrushes currently have the capability of more than one mode of operation. Each mode has a particular brush movement (amplitude and pattern of movement) and frequency to provide a desired effect. However, such modes operate for the entire length of a brushing event, which is typically two minutes.

Figure 1A:
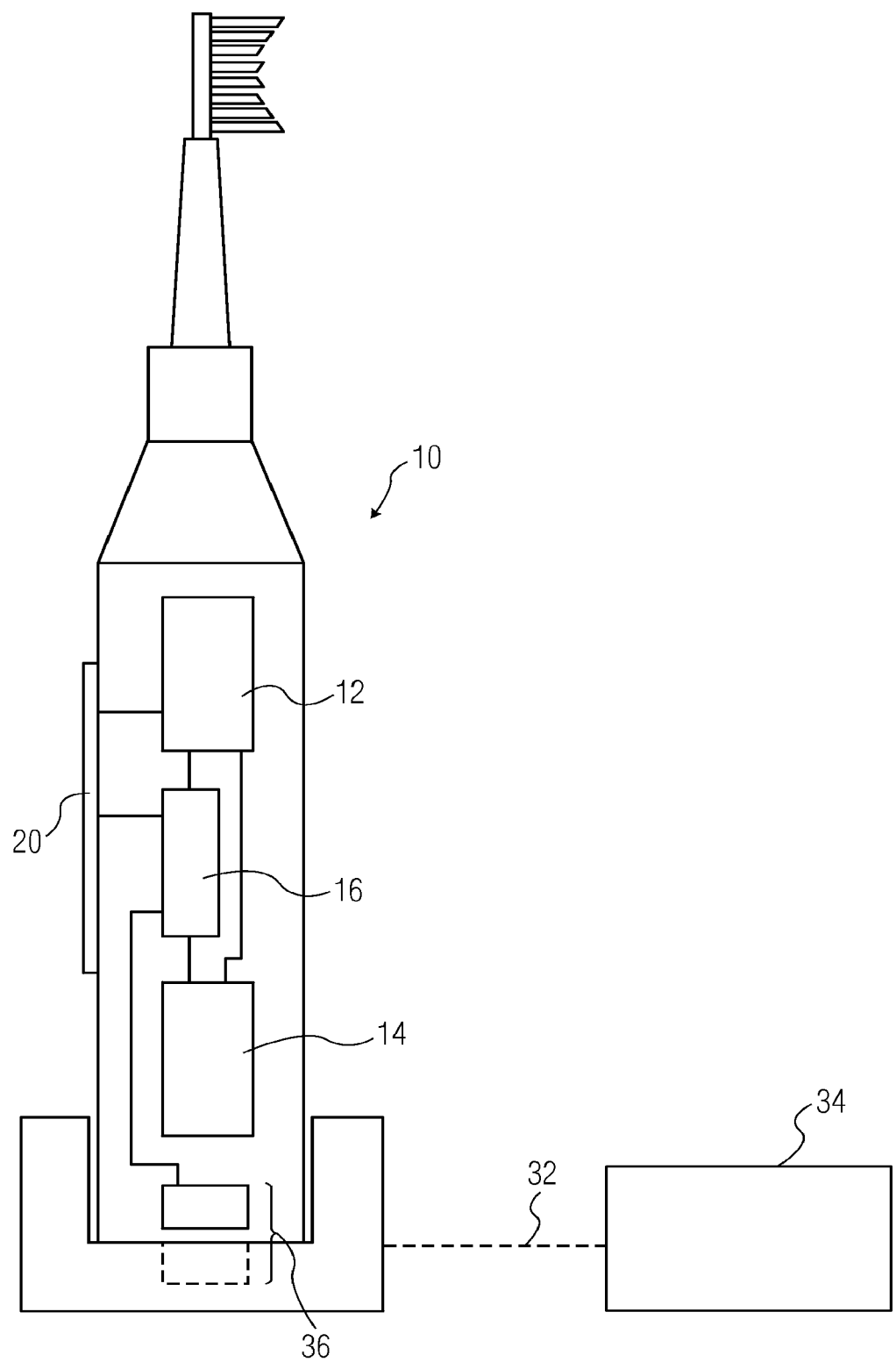
FIG. 1A is a simplified drawing of an electric toothbrush illustrating the structure of the present invention.
Figure 1B:
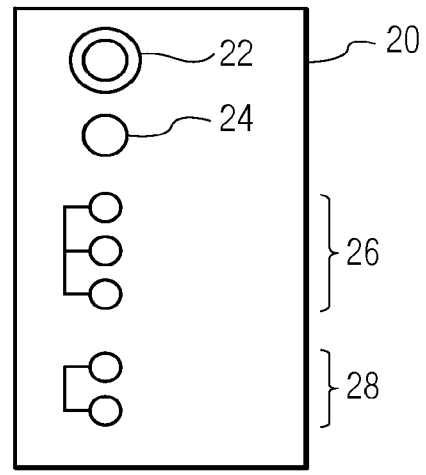
FIG. 1B is a diagram of an example of a user interface portion of an electric toothbrush.

FIGS. 1A and 1B show an arrangement where an electric toothbrush is programmed to include two or more modes which comprise a single brushing event. In such an arrangement, for each combined mode operation, two or more different modes of operation, each mode with a selected time, are programmed for a total time duration which is the same as for a single brushing event. Such combined modes, with selected times for each mode, are referred to hereinafter as mode/time profiles, or alternatively, routines, as used in FIG. 1B, meaning that a single brushing event comprises two or more individual modes, each of which has a pre-selected time duration within the normal brushing time.

One example of a mode/time profile would include first a low amplitude warm-up mode for 40 seconds, followed by a deep massage (pulsating) mode or a normal brushing mode for one minute, followed by a 20-second gentle mode to end the brushing event. Many combinations of different modes and times are possible.

The electric toothbrush 10 of FIG. 1 having such a capability is operated by a conventional motor 12, which is in turn powered by a rechargeable battery 14. The motor 12 is controlled by a programmed control assembly 16, which is capable of controlling the motor 12 to provide a selected amplitude and frequency of movement of the brushhead portion 18 of the toothbrush. The pattern of brushhead movement can also be controlled by the energizing signal applied to the motor. The brushhead movement could be arcuate, back and forth, pulsating (such as in a FIG. 8) or other types of movement. The amplitude and frequency of the brushhead movement can also be controlled, with different effects. As the toothbrush proceeds in its operation, an audible indication can be provided to the user indicating each change of specific mode.

The selection of a particular mode or mode/time profile for the toothbrush is controlled by a user interface 20. Each mode and mode/time profile available to the user is programmed at the factory into controller 16. An example of a user interface for mode or mode/time profile selection is shown in FIG. 1B, where the interface 20 includes an on/off button 22, a mode button 24, three different modes 26 which are selectable by the user, and two mode/time profiles (routines) 28, each of which comprise a combination of particular modes with, respectively, particular times.

The interface can be cycled through the three modes shown and the two mode/time profiles shown by use of the mode button 24. Again, this particular interface is for illustration, as a different number of modes can be programmed into the control assembly 16 and shown specifically on the interface, as well as a different number of mode/time profiles. The basic concept illustrated is that each mode/time profile is actually programmed into the control assembly and the user interface arranged so that by operating a single mode button, the interface unit cycles to the desired mode/time profile, which then is automatically initiated when the on/off button is thereafter operated. In another embodiment, the user can program a particular mode/time profile into the control assembly, to meet his/her specialized needs/desires.

The toothbrush can be programmed so that selection of a particular mode or mode/time profile can occur when the brush is in an off state, or when the brush has been turned on.

In another aspect of the arrangement of FIGS. 1A and 1B, a particular mode/time profile can be provided to the toothbrush through a link 32 from a device in a remote dental office 34 or other location, such as a user's computer. At the toothbrush, the desired mode/time profile information is received by a charge coil communication system, shown generally at 36. This arrangement is advantageous, because as particular mode/time profiles are discovered to have a particular beneficial result, which may be suited to the needs of a particular patient, a dentist (or the user) can construct a custom mode/time profile and provide it to the toothbrush following manufacture of the toothbrush.

The selection of a particular mode/time profile by a user can also be remembered by controller 16, so that a single user, by pushing the on/off switch, can have the toothbrush automatically go into the desired operation, without having to select it each time by operating the mode button as described above. This makes the use of a programmed mode/time profile even easier and more convenient to use.

Controller 16 can also remember the use of two (sometimes more) available mode/time profiles, such as by two separate users in a family, and produce those operating profiles in a sequence of operation of the toothbrush as a function of elapsed time between successive activations of the toothbrush. For instance, activating the brush a first time will result in a first mode/time profile, for a first user, and then activating the toothbrush a second time within a previous (known) elapsed time after the first activation will result in a second mode/time profile, for another user.

Still further, the controller 16 is also capable of remembering one mode/time profile at one time during the day, such as for a morning brushing, and a second mode/time profile at another selected time during the day, i.e. for an evening brushing, for a single user. This can also be done where more than two brushings occur, i.e. three brushings, each with a different mode/time profile.

Hence, having selected mode/time profiles programmed into the controller 16 results in a reliable, convenient arrangement for a user to accomplish a complex brushing operation pattern (profile) through simple, straightforward actions by the user, whether through operation of a single mode button or in some cases, just operating the on/off switch.

Figure 2:
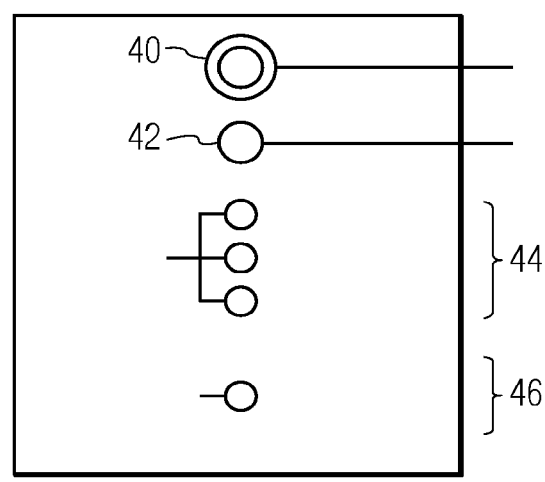
FIG. 2 is a diagram of a user interface portion of an electric toothbrush showing various operating modes, including an extended time indicator.

In another mode arrangement, the brushing time for a single event can be extended for an additional short period of time, e.g. 30 seconds, by one action of the user on a control interface portion of the toothbrush. Such a control interface is shown in FIG. 2, similar to that of FIG. 1B. In this interface, there is an on/off button 40, a mode button 42, three LEDs 44 indicating three different user modes and an LED 46 indicating an extended time mode, which could be manually or automatically set.

In the present control arrangement following the termination of a normal brushing event, i.e. following two minutes of brushing, the brush will turn off automatically. In the present arrangement, pressing the on/off button 40 following such termination results in an extended time of operation of the brush. While 30 seconds additional time might be typical, the time could be somewhat longer or shorter, e.g. in the range of approximately 20 40 seconds. The basic concept is to provide the capability of a specific mode of operation, which can be easily selected, which extends beyond the normal two-minute time. In order to accomplish this, the toothbrush controller 16 (FIG. 1) is programmed so that in response to the on/off button being operated within a certain time (for example, 15 seconds) after termination of a normal brushing event, the extended time mode turns on.

Figure 3A:
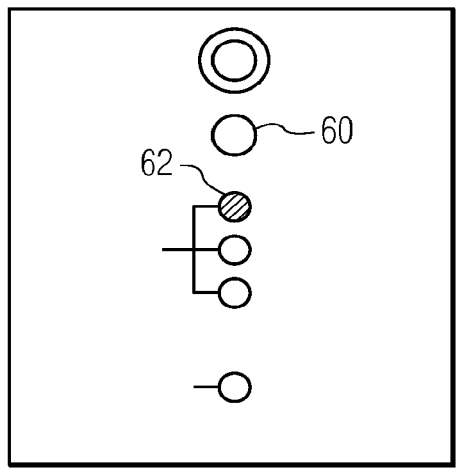
FIGS. 3A-3C are user interface diagrams showing a system for changing between various modes using a two-button control interface.
Figure 3B:
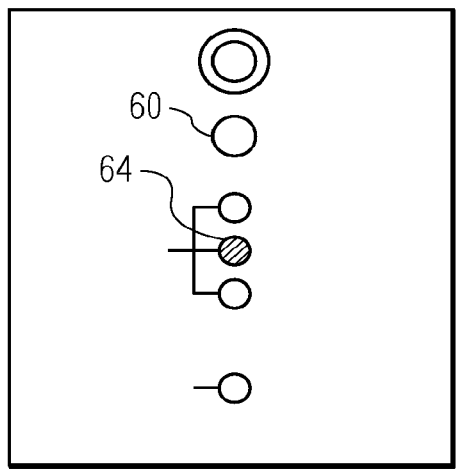
Figure 3C:
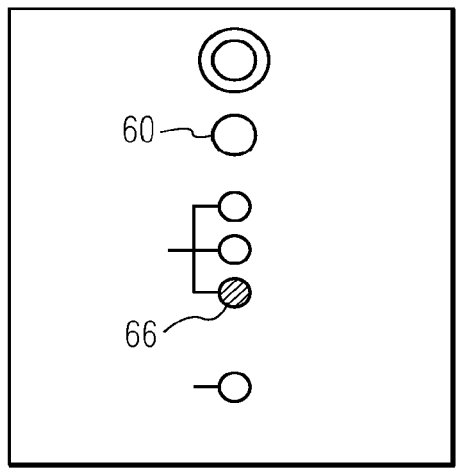
Figure 4A:
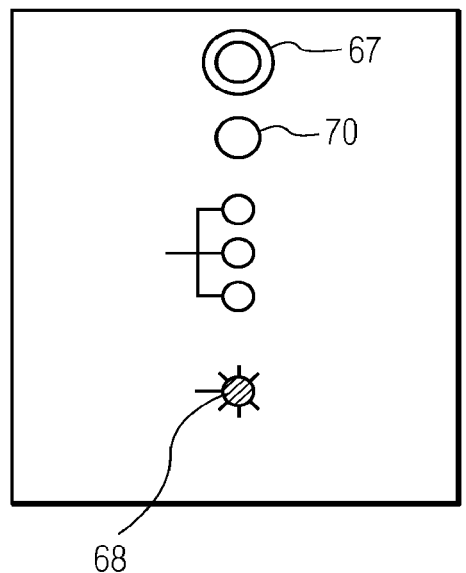
FIGS. 4A and 4B are interface diagrams showing a system for changing between an automatic and a manual extended time capability using the two-button interface of FIGS. 3A through 3B.
Figure 4B:
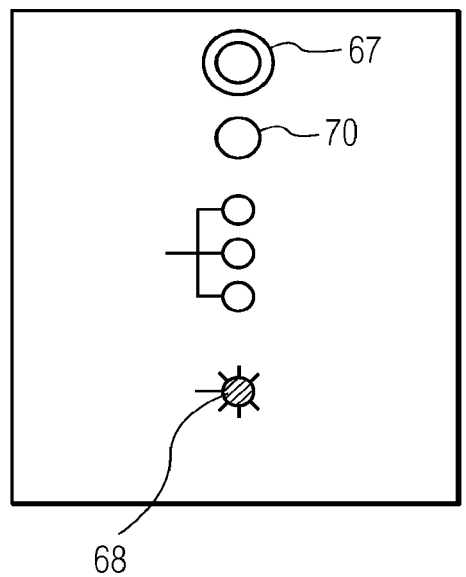

In one arrangement, the mode of operation of the toothbrush during the extended time period will be the same as the mode of operation during the normal (two-minute) brushing event. FIGS. 3A-3C show the sequence of how to operate mode button 60 to change the mode of normal operation of the toothbrush. Pushing the mode button 60 will change in sequence the operation of the toothbrush between the various possible modes. In the embodiment shown, this could be normal brushing operation, LED 62 is lit (FIG. 3A), gentle mode operation, LED 64 is lit (FIG. 3B), or massage mode of operation, LED 66 is lit (FIG. 3C). Other modes can be implemented, each with a particular brush action.

In a further development of the extended time/mode arrangement, the user has an opportunity to setup, i.e. establish, the extended time operating parameters. In a first setup step, the extended time arrangement can be implemented manually by pushing the on/off switch within a particular time after termination of a normal event, as discussed above, shown as "manual" operation on the interface, or it could be implemented automatically, in which the user automatically receives the additional time, without doing anything further with the interface. In addition, the actual mode of operation of the toothbrush during the extended time period can be selected by the user.

The selection of manual v. automatic and selection of a particular mode for the extended time period can be accomplished by the "setup" process illustrated in FIGS. 4A-4B, 5A-5D and 6 and described in the following paragraphs.

In a first step in the setup process, the extended time setting can be switched between manual and automatic. As indicated above, in the manual arrangement, the on/off switch must be operated as described above each time the extended time is desired. In the automatic arrangement, on the other hand, the extended time is provided automatically following each brushing event. In the programmed setup arrangement shown which is provided by the factory in the toothbrush, the user presses the on/off button 67 for a period of approximately three seconds in one embodiment. The time must be long enough to be a reliable indication that the setup process is desired by the user. The setup process can now begin. The manual/automatic LED 68 will blink and show the current state of extended time operation. In the embodiment shown, the color orange indicates the manual operation state, while green indicates the automatic state. Other colors can be used, as well as other visual indicators, such as blinking speed, to distinguish the two states of operation. Alternatively, two spaced LEDs could be used, one indicating manual and the other automatic. Operation of the mode button 70 when the manual/automatic LED 68 is blinking will change the extended time between manual or automatic as desired.

Figure 5A:
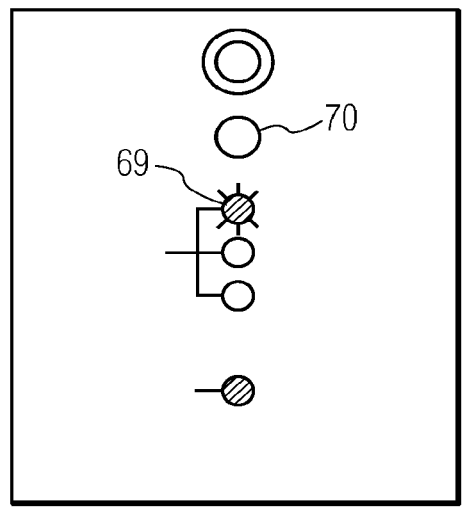
FIGS. 5A-5D are interface diagrams showing a system for selecting a mode for an extended time.
Figure 5B:
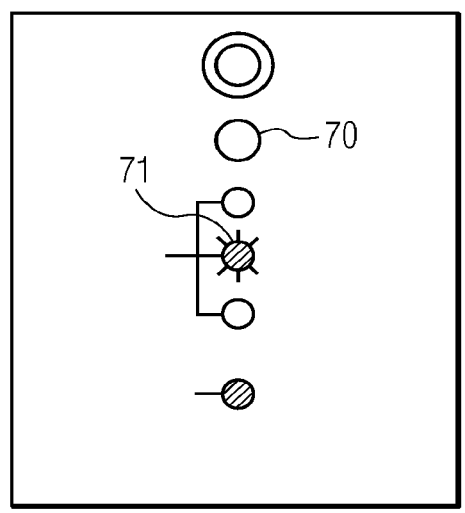
Figure 5C:
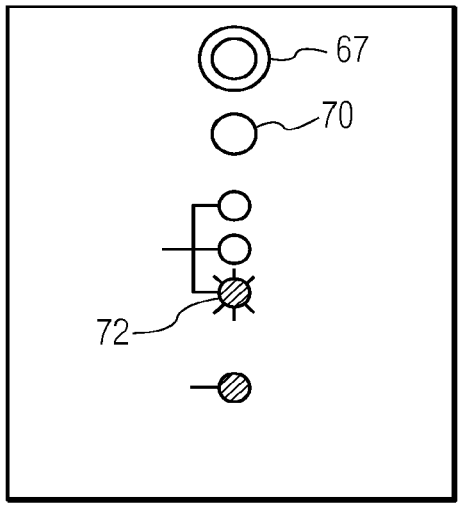
Figure 5D:
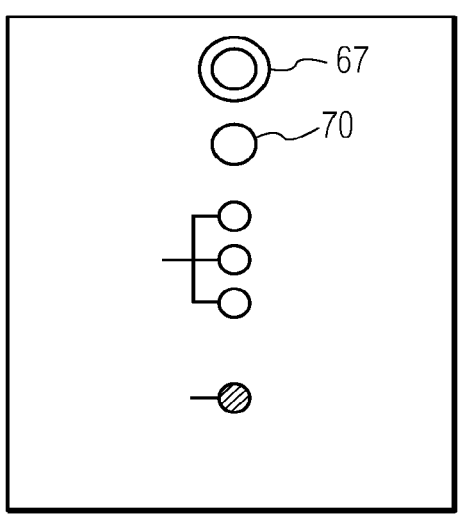

In a next setup operation, the user may select a mode for the extended time (period) which is different than the mode which is selected for the regular brushing period. This is advantageous, as it permits the user to have a particular brushing portion of a brushing event, for instance a gum massage, to finish the brushing. The mode for the extended time is changed by the user pressing the mode button during the setup process, which will then change the operating mode to a second mode, such as shown in FIG. 5B, illustrating a gentle mode (LED 71 is lit), and then to the next mode, which in FIG. 5C is a massage mode (mode LED 72 is lit). As the operational status changes, the immediate mode LED being selected begins to blink. At the last phase of the mode cycle, none of the mode LEDs is blinking, such as shown in FIG. 5D, which indicates that the extended time feature is in an "off" condition.

Figure 6:
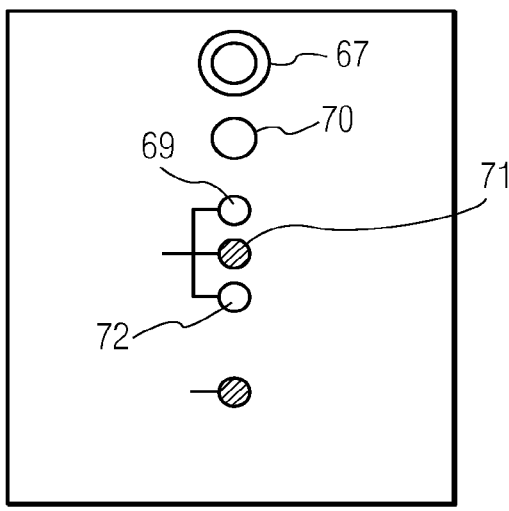
FIG. 6 shows the interface when a typical operation illustrated in FIGS. 5A-5D has been completed.
Figure 7A:
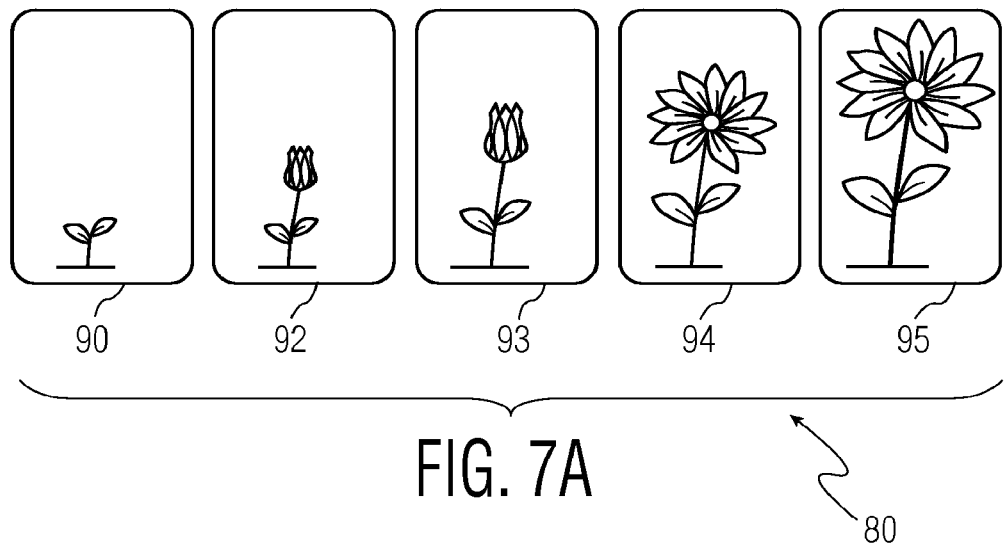
FIGS. 7A-7B are simplified diagrams showing a brushing system for use with children.
Figure 7B:
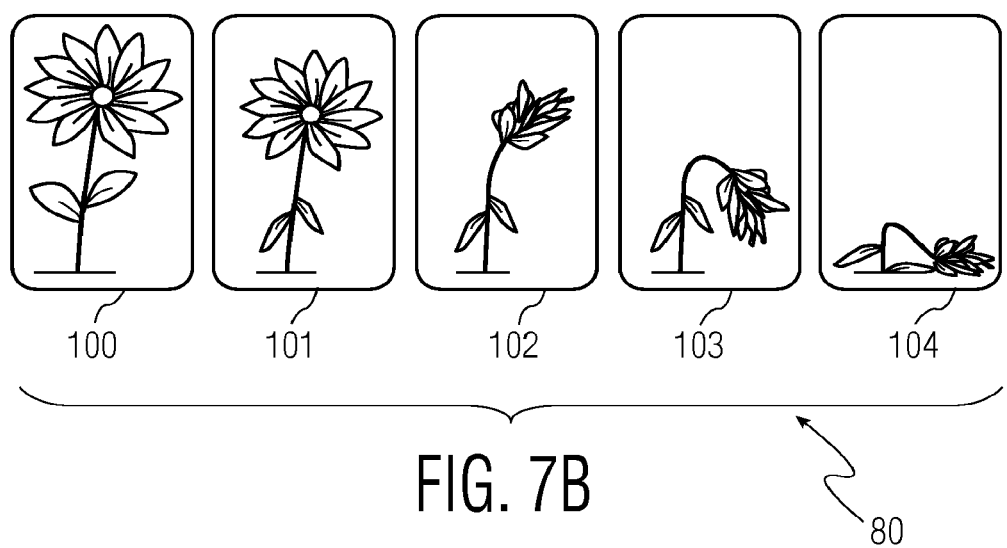

After the operational mode for the extended time has been selected by the user during the extended time setup process, the on/off button 67 is operated; this results in the chosen setup being displayed by the interface LEDs for a selected period, for instance 30 seconds. FIG. 6 shows the result of one extended time setup process, in which the manual/automatic LED is lit, either orange or green, and the operation of the toothbrush will be in the gentle mode during the extended time period.

Although not specifically illustrated, the setup procedure could include a capability of the user to set a specific extended time period. A default time of 30 seconds could be included.

FIGS. 7A, 7B, 8 and 9A-9D show an arrangement which is specifically directed toward encouraging children in brushing and to provide corresponding information to parents to monitor their children's brushing habits and/or progress. In one embodiment, illustrated in FIGS. 7A and 7B, the toothbrush system includes a display 80 which illustrates use of the toothbrush against a selected standard, as described below. This arrangement shows a toothbrush in a specialized mode of operation in which performance of a user with the toothbrush is displayed, rather than changing the operation of the toothbrush. It is thus a user-interface mode. The communication between the user of the toothbrush and a separate display which is visible to the user could be done by a wireless (RF link) or a wire link. This display could also be on-board the toothbrush, such as in the handle.

In this embodiment, for instance, a performance standard of two minutes of actual brushing use is established, and a flower is used to illustrate brushing progress. When the brush is turned on, the flower is in an initial, early condition, such as illustrated at 90 in FIG. 7A. As the time during which the brush is actually being used increases from the initial turning on of the brush, the flower gradually opens in a natural sequence of blooming, until at two minutes, it reaches its fully bloomed state. This progression is illustrated in display panels 92-95. More than five panels can certainly be used to promote step-by-step progress toward brushing for a full two minutes. The basic concept is to use an animated display, such as a flower, progressing from an initial (bud) condition to full flowering. This is an encouragement to the user to continue to brush to see the flower develop to its full bloom.

Alternatively, if the toothbrush is not used for the full two minutes, the display of the flower can move in a negative direction. This is illustrated in the displays of 100-104. The degree to which the flower regresses, in the illustration of the display panels, will depend upon the difference between the actual use of the toothbrush during one event and the desired time of use.

While a flower has been shown and described as one specific embodiment/illustration of the invention, other illustrations can be used. One example would be a rocket ship going from the earth to the moon, in which use of the toothbrush for the full two minutes will result in a satisfactory landing on the moon. Other similar illustrations would certainly occur to one skilled in the art, including animals and various machines. The animation again provides a visual indication of the association between actual use and a desired type of use for the benefit of the young user of the toothbrush.

The same principle can also be used where the standard to be attained encompasses more than time of brushing, such as for instance brushing pressure or appropriate movement of the brush between the various quadrants of the mouth. The progress in the illustration panels, both positively and negatively, can be quite sophisticated with different programming branches and illustration panels, depending upon the overall compliance of the child with various brushing standards. Again, these standards could be overall brushing time, brushing pressure, and coverage, with appropriate times, of all of the areas of the mouth, among others.

Figure 8:
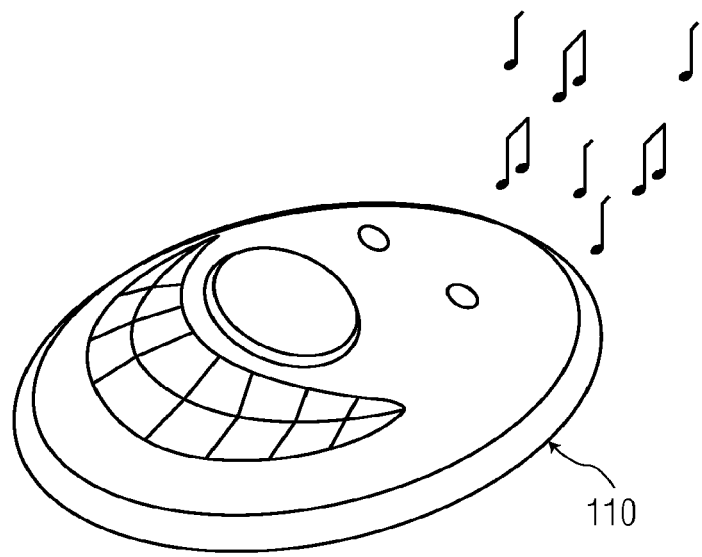
FIG. 8 is a diagram showing another brushing system for use with children.
Figure 9A:
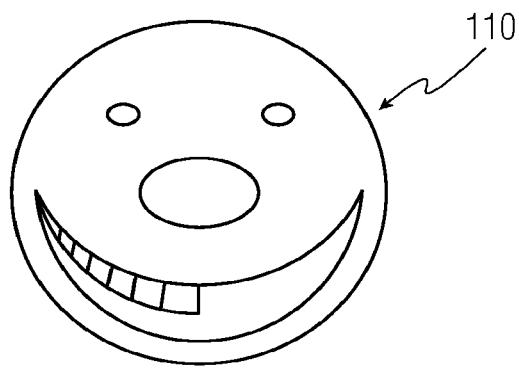
FIGS. 9A-9D are a sequence of diagrams showing the operation of the system of FIG. 8.
Figure 9B:
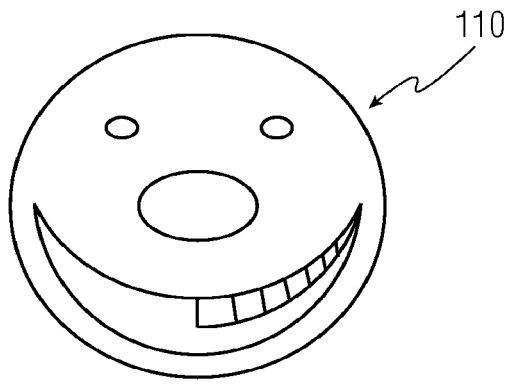
Figure 9C:
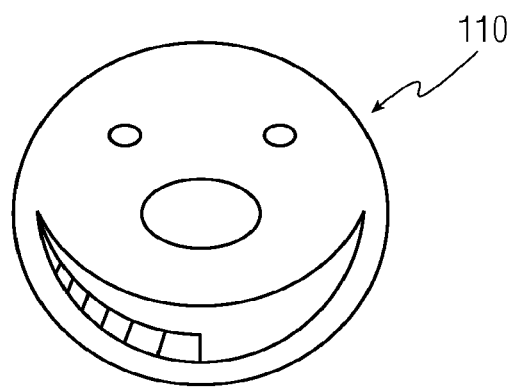
Figure 9D:
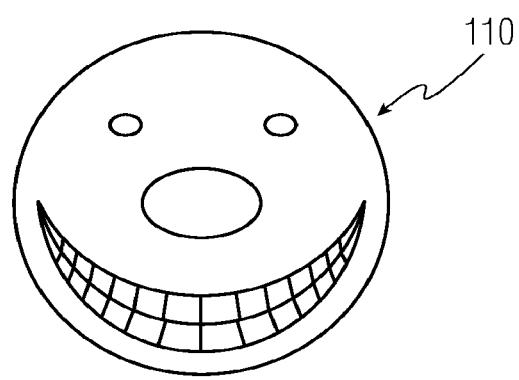
Figure 10:
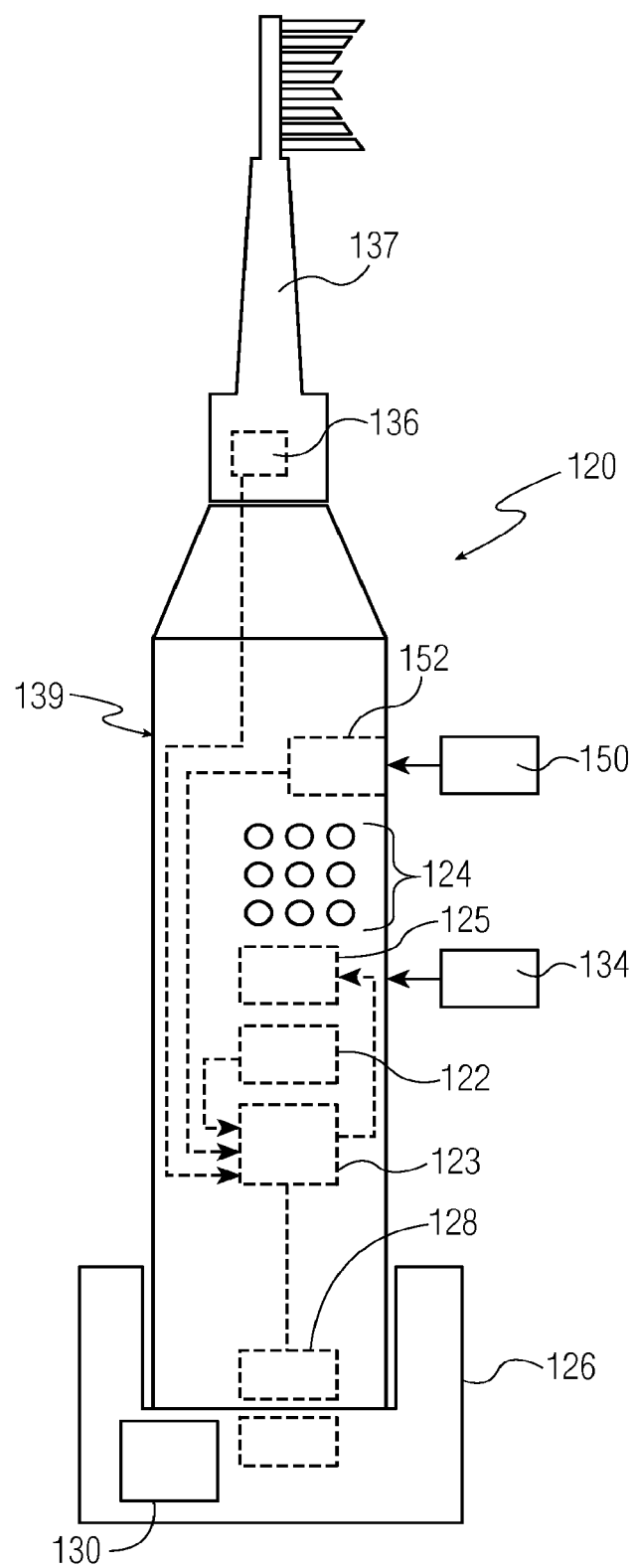
FIG. 10 is a schematic view of a toothbrush with various embodiments for changing operating characteristics of the toothbrush as children get older.
Figure 11:
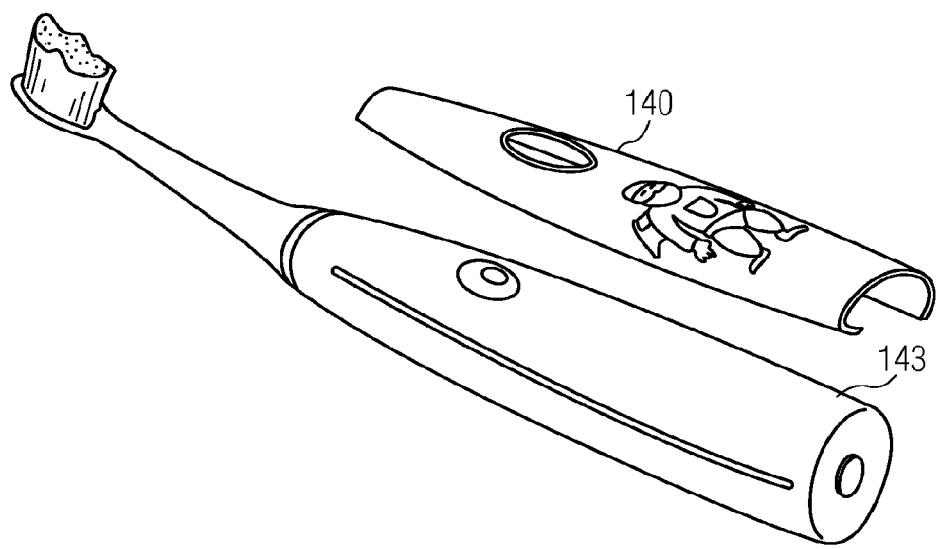
FIG. 11 is a schematic view of a toothbrush with a skin member for changing operating characteristics of the toothbrush.

A variation of this arrangement is shown in FIG. 8 and FIGS. 9A-9D. FIG. 8 shows a display device 110 with a humorous face displaying a full mouth of teeth. This device can be used with or without musical accompaniment. This also could be a separate display device or on the handle of the toothbrush. As shown in FIGS. 9A-9D, coverage of the various quadrants of the mouth can be illustrated on the display as movement of the brush between the various quadrants occurs. FIGS. 9A-9D show one sequence of coverage of the brush, again illustrating with particularity the use of the toothbrush by a child.

The information concerning actual brushing use of the toothbrush by a child can be accumulated as data and then displayed by the toothbrush system for the convenience of the parents or other interested person, such as a dentist. In this mode, which is selectable by the parent, the use of a toothbrush, including particularly brushing times for individual children, can be readily displayed for the parent's information for a selected time period, such as brushing during the immediate day, the previous day or several previous days or more. The parent receives immediate feedback in the form of actual data for monitoring a child's brushing performance.

At the same time the apparatus is providing visual and audio encouragement and stimulation for the child to comply with a desired brushing schedule.

Hence, various operating mode arrangements for an electric toothbrush have been disclosed. These modes involve the particular operation of the toothbrush, including movement of the brush and frequency. In another mode, variation of brushing time is provided. A user interface/performance arrangement is also disclosed which is designed to provide encouragement and stimulation to a child to maintain desired brushing habits.

FIGS. 10-14 are directed toward a system by which the performance characteristics of a power toothbrush change, as appropriate and in a predetermined manner, for use of the toothbrush by a child, over a span time, typically several years. The initial settings could be suitable for a young child, such as 3 or 4 years, or higher if desired, and then change periodically to the point where the child is able to readily tolerate full performance of the toothbrush. This will typically be sometime after the child has their adult teeth.

A power toothbrush is illustrated generally at 120. In one embodiment, the power toothbrush includes a stored program 122 which includes performance/operating characteristics for the power toothbrush at various selected ages. A microprocessor control 123 operates the toothbrush through a motor assembly 125, which can be any of various known arrangements. These performance characteristics include, for example, amplitude of movement of the brushhead, frequency of brushhead movement and brushing time. Other characteristics can also be included. One or more of these operating characteristics can be varied for each different age level. The performance characteristics could also include an adaptation routine for load, based on user reaction. The brush could sense user pressure of the brush against the teeth and adjust the amplitude a selected amount to compensate for the actual use of the brush. For example, if the user is pressing the brush bristles too firmly against the teeth, the amplitude could be increased a selected amount, while if the user produces a less firm or slight contact with the teeth, the amplitude of motion could be decreased or vice versa.

In stored program 122, the specific value stored therein of each performance characteristic for the toothbrush for the various ages is in accordance with known data relative to children and teens, i.e. appropriate performance settings related to age. The operation of the toothbrush is thus specifically adapted in steps related to particular ages, until the user is ready for full power operation. One or more of the various operating characteristics can be changed at the various preselected age intervals, for example every two years. The changes, however, can be made at other ages.

The initial level of operation, or the child's age at initial use, can be entered into the toothbrush through various ways. This initializes the stored program at a selected level, e.g. 4 years old. One way is by use of a plurality of buttons 124 on the toothbrush itself. Another way is by communication between a charger 126 for the toothbrush and the toothbrush through a charge coil 128 or another independent coil in the toothbrush and corresponding coil in the charger. The charger could include a keypad or touch screen 130 for entry of the desired information. A still further way is a conventional RFID tag 134 which can be secured or brought into proximity with the toothbrush to initialize the stored program at a particular age/performance level. The RFID tag could be contained in a sticker which could be adhered to the toothbrush. In each case, the microprocessor in the toothbrush will recognize the information provided through the various entry means to produce the selected levels of performance characteristics for a particular age/level. The toothbrush will then run with the selected performance characteristics.

The various entry means described above, besides initializing the stored program 122 at a particular level, could be used to input the actual performance characteristics for a particular entry level age. This could also be done at the other ages as well. In such an arrangement, the performance information is provided from a source exterior to the toothbrush, instead of an internal stored program.

In another arrangement, entry or operating information 136 could be provided by a head portion 137 for the toothbrush, which is removable from a handle portion 139. Different heads could have operating characteristics for particular ages. The replacement of one head corresponding to a particular age by another head for a different age will result in change of operating characteristics for the toothbrush, as information is provided from the head to the microprocessor control 123 for the toothbrush. In addition, it is possible to have an entirely new toothbrush with new performance characteristics for each selected age level.

Figure 12:
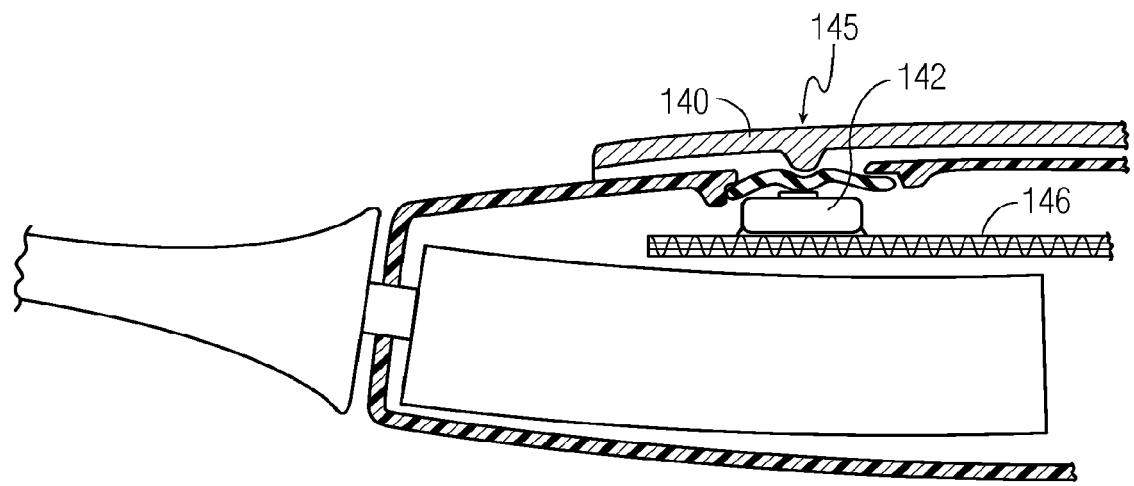
FIGS. 12-14 are cross-sectional views of the skin member of FIG. 11, showing various ways of changing the operating characteristics of the toothbrush or initiating operation thereof.

In still another embodiment as shown in FIGS. 11-14, various skin assemblies could be used with a power toothbrush, with each skin member 140 having adaptive elements to initialize/change the performance characteristics for a selected age level. The skin member could cover the entire handle 143 or just a portion of it. The skin member can be attached by a snap-on or slide-on arrangement, Velcro, adhesive, magnetic or other arrangement. The skin assembly 140 could be designed to appeal to a particular age, with age-appealing designs/configurations. Referring to FIG. 12, the skin member 140 could be used to change the operating characteristics through contact elements 142 on an internal surface of the skin member, which would interact with corresponding elements on the toothbrush, in particular elements on a PC board 146, activated by pushing on a portion 145 on the skin member. Alternatively, the switch to activate the device can be entirely within the skin member, communicating with the handle through an RFID element or similar system.

Figure 13:
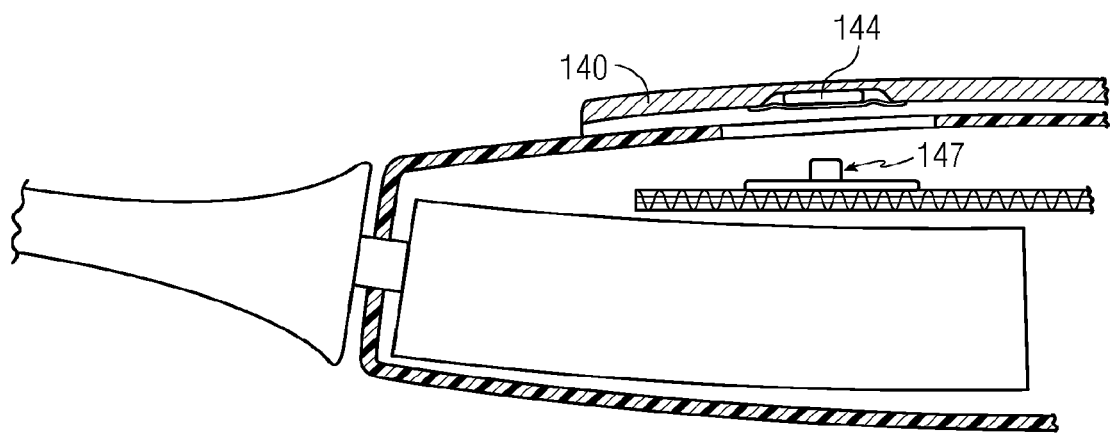
Figure 14:
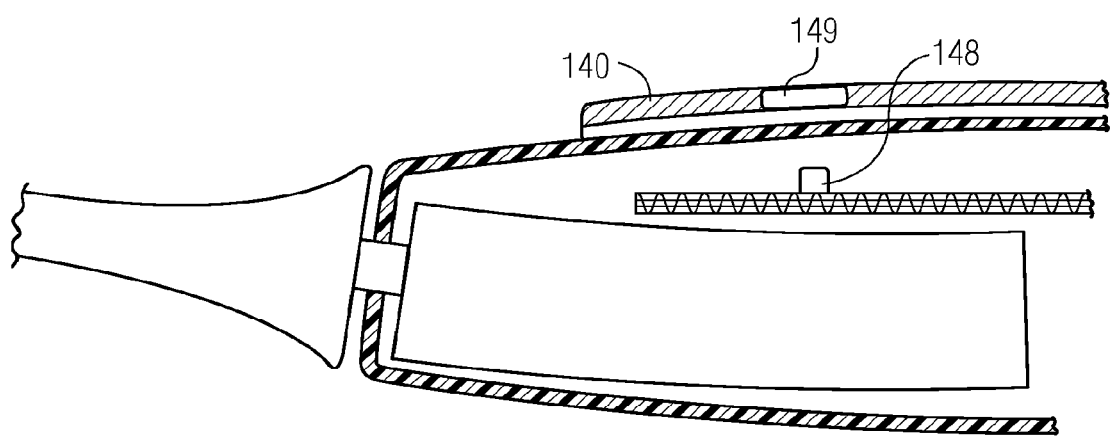

Referring to FIG. 13, the skin member 140 could alternatively contain an RFID tag 144 (RFID chip and antenna) in combination with an RFID receiver and antenna 147 in the toothbrush which would provide the appropriate initializing information from the stored program or the actual performance characteristics. In still another embodiment, shown in FIG. 14, a skin member 140 could use a Hall-Effect arrangement with a sensor 148 in the handle or a PC board and a magnet 149 in the skin member.

The skin could also contain a series of magnets that are sensed by corresponding elements in the handle which in turn would set the desired performance characteristics.

In a further embodiment, the initializing information or operating characteristics could be provided in a cartridge 150, which would be insertable into a receiving port 152 in the toothbrush. The receiving port could be located anywhere on the handle, including the base. The receiving port would be connected to the microprocessor 123. The individual cartridges could, for instance, be provided successively by a dentist, at selected ages for the user.

The above system of FIGS. 10-14, with its different embodiments, can be used with a power toothbrush so it will operate in a particular manner appropriate for various ages of children. Hence, the advantages of a power toothbrush can be obtained for children from a relatively young age up to the point in time when the child is ready for an adult power toothbrush.

Although various embodiments of the invention have been disclosed for purposes of illustration, it should be understood that various changes, modifications and substitutions may be incorporated in such embodiments without departing from the claims which follow.

What is claimed is:

1. A system for extending the time of automatic operation of an electric toothbrush, comprising:
a control system for the toothbrush which controls the operation of a brushhead portion of the toothbrush, the control system configured to have at least two operating modes comprising a normal brushing mode and an extended brushing mode,
said normal brushing mode having a first predetermined amount of time for brushing operation of the toothbrush, wherein said control system is configured to automatically terminate brushing operation after said first predetermined amount of time for brushing operation,
said extended brushing mode having a pre-programmed capability of providing a second predetermined amount of additional time for brushing operation of the toothbrush within a predetermined period of time subsequent to the termination of the normal brushing mode, the second predetermined amount of additional time being substantially less than the first predetermined amount of time of the normal brushing mode,
wherein the control system is configured to provide the additional time for brushing operation of the toothbrush during the extended brushing mode only upon actuation of a control element by a user within said predetermined period of time following termination of the normal brushing mode.

2. The system of claim 1, wherein the amount of additional time is configured, in response to a setup command provided by the user to the control system.

3. The system of claim 1, wherein the additional time is within the range of 20 to 40 seconds.

4. The system of claim 1, wherein the additional time is approximately thirty seconds.

5. The system of claim 1, wherein the control element is an on/off switch for the toothbrush.

6. The system of claim 1, wherein said predetermined period of time for actuation of the control element is within the range of 0 to 10 seconds.

7. The system of claim 1, wherein the toothbrush includes a user interface and wherein the control system is programmed to permit selection of a mode of operation of the toothbrush during the additional time period which is different than the mode of operation during an immediate past brushing event.

* * * * *